United States Patent [19]

Taniguchi

[11] Patent Number: 5,262,304
[45] Date of Patent: Nov. 16, 1993

[54] METHOD FOR OPTICAL MEASUREMENT OF BILIRUBIN AND REAGENT THEREFOR

[75] Inventor: Seiichi Taniguchi, Neyagawa, Japan

[73] Assignee: Nippon Shoji Kabushiki Kaisha, Osaka, Japan

[21] Appl. No.: 629,454

[22] Filed: Dec. 18, 1990

[30] Foreign Application Priority Data

Dec. 18, 1989 [JP] Japan .................. 1-327523

[51] Int. Cl.$^5$ .................. C12Q 1/26; G01N 33/00
[52] U.S. Cl. .................. 435/25; 435/4; 435/189; 435/191; 436/12; 436/97; 436/100; 436/101
[58] Field of Search .................. 435/25, 189, 4, 191; 436/12, 97, 100, 101

[56] References Cited

U.S. PATENT DOCUMENTS

| | | | |
|---|---|---|---|
| 4,211,844 | 7/1980 | Wu | 435/25 |
| 4,571,383 | 2/1986 | Takayama et al. | 435/25 |
| 4,600,689 | 7/1986 | Matsui et al. | 435/25 |
| 4,895,799 | 1/1990 | Kruse-Müller et al. | 435/25 |

FOREIGN PATENT DOCUMENTS

| | | |
|---|---|---|
| 0197439 | 10/1986 | European Pat. Off. . |
| 59-130198 | 11/1984 | Japan . |
| 62-112068 | 10/1987 | Japan . |
| 2115926 | 9/1983 | United Kingdom . |

OTHER PUBLICATIONS

Simunek et al., *Chemical Abstracts*, vol. 97, Ref. No. 35567v, 1982.
Doumas et al., *Clinical Chemistry*, vol. 31, No. 11, pp. 1779–1789, 1985.
Johnson et al, *Clinical Chemistry*, vol. 23, No. 7, pp. 1321–1327, 1977.
Worth et al, *The Journal of Laboratory and Clinical Medicine*, vol. 70, No. 2, pp. 352–354, 1967.
Corns et al., *Chemical Abstracts*, vol. 108, Ref. No. 18708v, 1988.
Japanese Patent First Publication No. 112068/1987, with English language summary.
*Nature*, vol. 195, Aug. 4, 1962, p. 490, "Quantitative Determination of Bilrubin and other Tetrapyrrols".
Patent Abstracts of Japan, vol. 8, No. 251, Nov. 16, 1984, 59-130198, Jul. 26, 1984.
Patent Abstracts of Japan, vol. 11, No. 328, Oct. 27, 1987, 62-112068, May 23, 1987.
Worth et al., "Basic zinc test for urine bilirubin", *The Journal of Laboratory and Clinical Medicine*, vol. 70, No. 2, Aug. 1967, pp. 352–354.

*Primary Examiner*—Michael G. Wityshyn
*Assistant Examiner*—Abdel A. Mohamed
*Attorney, Agent, or Firm*—Wegner, Cantor, Mueller & Player

[57] ABSTRACT

A method for optical measurement of bilirubin which comprises reacting a bilirubin-containing sample with a zinc compound, a coloring agent and bilirubin oxidase in a buffer, wherein a stable green pigment having a large molecular extinction coefficient is formed by the action of the zinc compound and thereby bilirubin in the sample can be measured specifically, and a reagent useful therefor. Said method and the reagent are useful for clinical test of total bilirubin and direct bilirubin in serum.

9 Claims, 7 Drawing Sheets

METHOD FOR OPTICAL MEASUREMENT OF BILIRUBIN AND REAGENT THEREFOR

The present invention relates to a method for optical measurement of bilirubin and a reagent used therefor, which are useful for clinical tests. More particularly, it relates to a method for optical measurement of bilirubin, especially total bilirubin and direct bilirubin, which comprises reacting a bilirubin-containing sample with a zinc compound, a coloring agent and a bilirubin oxidase in a buffer, and a reagent used therefor.

PRIOR ART

There are two types of bilirubin, i.e. conjugate type bilirubin (also referred to as "direct type bilirubin" or merely as "direct bilirubin") and non-conjugate type bilirubin (also referred to as "indirect type bilirubin" or merely as "indirect bilirubin"). Direct bilirubin and indirect bilirubin are collectively called total bilirubin. In clinical tests, there are usually measured total bilirubin and direct bilirubin, and indirect bilirubin is calculated by deducting the amount of direct bilirubin from that of total bilirubin. These two types of bilirubin have the following relation with diseases. For example, in acute obstructive jaundice, direct bilirubin is increased in blood; and in hemolytic jaundice, indirect bilirubin is increased in blood. Thus, it is essential for clinical test to accurately measure total bilirubin and direct bilirubin.

The serum bilirubin is usually measured by a colorimetry with a diazo reagent according to the method of Malloy-Evelyn or the method of Michaëlsson. However, these methods are disadvantageous in that the reaction is not specific and the procedures are much complicated.

Recently, a method for measuring total bilirubin using bilirubin oxidase derived from *Agaricus bisporus* (Japanese Patent Second Publication No. 11194/1983), a method using bilirubin oxidase derived from a species of genus *Myrothecium* (Japanese Patent First Publication No. 17999/1984), a method using bilirubin oxidase M-1 derived from *Trachyderma tsunodae* (Japanese Patent First Publication No. 249060/1985) and the like. In addition, a method for enzymatic measurement of direct bilirubin has also been developed (Japanese Patent Second Publication No. 44000/ 1986). The enzymatic method, which comprises reacting a bilirubin-containing sample with bilirubin oxidase and optically measuring a decrease of yellow color of bilirubin due to the enzymatic reaction, is more advantageous than the chemical method in that bilirubin is accurately measured because of specificity of reaction, but it is disadvantageous in that it requires a blank test.

There is also developed a colorimetric method for measuring total bilirubin in which a coloring agent is used for development of bilirubin in the enzymatic reaction; for example, a method for measuring bilirubin which comprises reacting a bilirubin-containing sample with 3-methyl-2-benzothiazolinone-hydrazone (MBTH) as a coloring agent and bilirubin oxidase M-1 to form a red pigment and then acidifying the reaction solution with a strong acid (e.g. HCl, etc.) to form a blue pigment, followed by optical measurement of the blue pigment (Japanese Patent First Publication No. 31096/1986), a similar method for measuring bilirubin using other bilirubin oxidase (Japanese Patent First Publication No. 112068/1987), and the like.

Furthermore, there is also proposed a colorimetric method for measuring bilirubin by chemical development with ferric chloride in a strong acid [J. Fog. Nature, 195, 490 (1962)].

These colorimetric methods for measuring bilirubin do not require a blank test of sample, and hence, are more advantageous than the enzymatic method in which a decrease of yellow color of bilirubin is measured. However, these methods disadvantageously involve the acidification of the reaction solution, and as a result, the procedure becomes more complicated, less speedy and not suitable for automatic analysis. In addition, an accelerator for converting indirect bilirubin into direct bilirubin (e.g. sodium cholate, sodium dodecyl sulfated (SDS), etc.) is used for measurement of total bilirubin. However, the above agent is insoluble in the strongly acidic reaction solution, and hence, the solution becomes opaque and incapable of measurement of total bilirubin. Accordingly, neither total bilirubin nor direct bilirubin in patient serum can be measured by the colorimetric method.

As mentioned above, all the conventional methods for measuring bilirubin are disadvantageous. That is, the chemical method is disadvantageous in that the reaction is non-specific and the procedure is complicated. As to the enzymatic method, although the reaction specificity is higher than with the chemical method, the method requires the blank test of sample. The colorimetric method using the coloring agent such as MBTH is more advantageous than the enzymatic method in that it does not require the blank test of sample. However, the method cannot suitably be designed for automatic analysis since each reagent used in the method should be used separately from the viewpoint of stability, i.e. the first reagent of a buffer containing a coloring agent, the second reagent containing bilirubin oxidase and the third reagent of an acidic solution. Moreover, the procedure in the colorimetric method is conducted in three steps, and hence, is complicated and is not speedy. In addition, the accelerator for converting indirect bilirubin into direct bilirubin such as sodium cholate and SDS cannot be used in the colorimetric method due to its insolubility in the final reaction solution which is made acidic with a strong acid, and therefore, the method is incapable of measuring total bilirubin and direct bilirubin. Therefore, it is earnestly desired to develop an improved method in which total bilirubin and direct bilirubin can easily be measured without the above-mentioned disadvantages.

SUMMARY DESCRIPTION OF THE INVENTION

Under the circumstances, the present inventors have extensively studied in order to develop an improved method for measuring bilirubin without the above-mentioned disadvantages, and as a result, have found that bilirubin can be measured by easily reacting a bilirubin-containing sample with a coloring agent and bilirubin oxidase in the presence of a zinc compound in the above-mentioned colorimetric method using an enzyme so that a stable green pigment is formed without making the reaction solution acidic with a strong acid and that both total bilirubin and direct bilirubin can be measured by adjusting the pH of the buffer to a suitable range.

An object of the invention is to provide a method for optical measurement of bilirubin which comprises reacting a bilirubin-containing sample with a zinc compound, a coloring agent and bilirubin oxidase in a suitable buffer. Another object of the invention is to provide a method for measuring total bilirubin using a buffer at pH 6.0 to 9.0. Still another object of the invention is to provide a method for measuring direct bilirubin using a buffer at pH 3.0 to 4.5. A further object of the invention is to provide a reagent useful for measuring bilirubin in the methods of the invention. These and other objects and advantages of the present invention will be apparent to those skilled in the art from the following description.

DETAILED DESCRIPTION OF THE INVENTION

Figure 1:
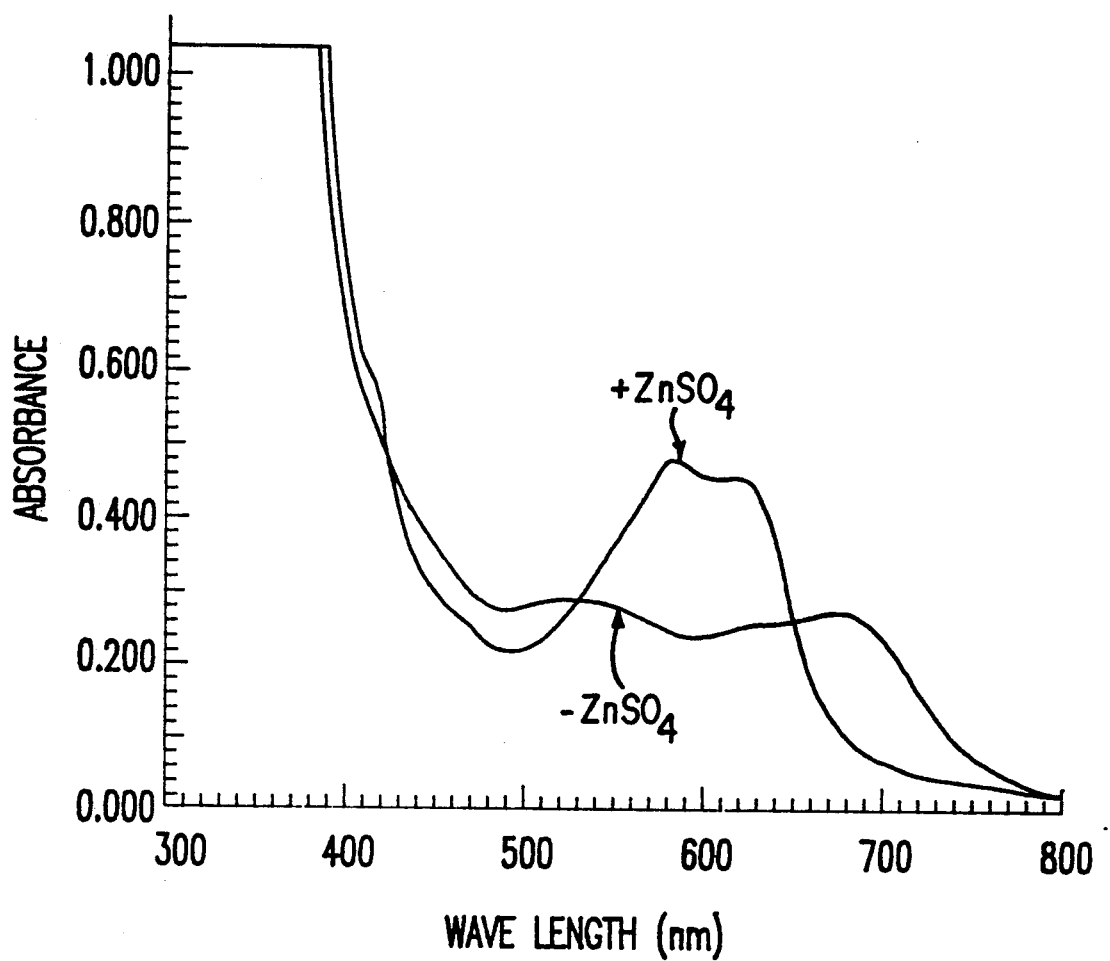
FIG. 1 is an absorption curve in measurement of total bilirubin in a sample by the method of the present invention.

According to the method of the present invention, bilirubin is measured by adding a buffer containing a zinc compound and a coloring agent to a bilirubin-containing sample, incubating the reaction solution, adding bilirubin oxidase to the reaction solution to form a green product and then measuring the product by colorimetry. Unlike such conventional colorimetric method as described in Japanese Patent First Publication No. 112068/1987, this method allows for formation of a stable green pigment having a large molecular extinction coefficient without acidification of the reaction solution with a strong acid. In addition, unlike the conventional colorimetric method in which a bilirubin-containing sample is reacted with bilirubin oxidase and a coloring agent without any zinc compound, which shows disadvantageously absorption interference due to non-specific reaction, the method of the present invention wherein the reaction is conducted in the presence of a zinc compound allows for accurate measurement of bilirubin since the zinc compound has an action to eliminate such absorption interference.

The zinc compound used in the method of the present invention may be any substance containing zinc, including, for example, zinc oxide compounds (e.g. zinc oxide, zinc hydroxide, etc.), inorganic acid salts of zinc (e.g. zinc sulfate, zinc nitrate, etc.), organic acid salts of zinc (e.g. zinc acetate, zinc lactate, etc.), zinc halides (e.g. zinc fluoride, zinc chloride, zinc bromide, zinc iodide, etc.), zinc cyanide, and the like. The zinc compound is used at a suitable concentration. In order to yield a green pigment having a large molecular extinction coefficient, the zinc compound is used at a concentration in the reaction solution ranging from 0.02 to 3.0 mM, preferably from 0.05 to 2.1 mM for measurement of total bilirubin, from 0.1 to 3.0 mM, preferably from 0.4 to 2.1 mM for measurement of direct bilirubin.

Examples of the coloring agent which can be used for the method of the present invention are, in addition to the above-mentioned MBTH, 2-hydrazinobenzothiazole, 1-hydrazinophthalazine hydrochloride, and the like, all of which can form a stable green pigment. The coloring agent is suitably used in an amount effective for color formation, usually in a range from 0.3 to 3.0 mM.

The buffer used in the method of the present invention may be any known buffer insofar as it does not form a chelate with the zinc compound. However, the buffer with a different pH range is employed depending on what kind of bilirubin, total bilirubin or direct bilirubin, is to be measured.

For measurement of total bilirubin, the buffer with pH from 6.0 to 9.0 is employed. Examples of the buffer are a Good's buffer such as N-(2-acetamide)-2-aminoethane-sulfonic acid (ACES) buffer, 3-(N-morpholino)-2-hydroxy-propanesulfonic acid (MOPSO) buffer, 3-(N-morpholino)-propanesulfonic acid (MOPS) buffer, 3-[N-tris(hydroxy-methyl)methylamino]-2-hydroxypropanesulfonic acid (TAPSO) buffer and the like, having pH from 6.0 to 9.0. The buffer preferably contains the accelerator for converting indirect bilirubin into direct bilirubin such as sodium cholate, SDS and laurylbenzene sulfate (LBS) so that the reaction proceeds efficiently in the method for measurement of total bilirubin.

The buffer for measurement of direct bilirubin has, a pH from 3.0 to 4.5. Examples of the buffer are lactic acid-sodium lactate buffer, tartaric acid-sodium tartrate buffer, glycine-hydrochloric acid buffer, acetic acid-sodium acetate buffer, sodium acetate-hydrochloric acid buffer, and the like. Citric acid buffer and phosphoric acid buffer cannot be used for measurement of direct bilirubin since zinc is blocked by these buffers.

Bilirubin oxidase may be any known enzyme, including bilirubin oxidase derived from a species of genus *Myrothecium*, bilirubin oxidase produced by Trachyderma tsunodae, and the like. Bilirubin oxidase is suitably used in an amount effective for showing the desired enzyme activity, usually in an amount from 0.04 to 10 Units/ml, preferably from 0.08 to 4 Units/ml for measurement of total bilirubin, from 0.04 to 10 Units/ml, preferably from 0.4 to 8 Units/ml for measurement of direct bilirubin.

A reaction promoting agent can also be used if necessary and the use of the reaction promoting agent can reduce the amount of bilirubin oxidase. For example, when 10 to 500 μM of potassium ferricyanide as the reaction promoting agent is added to the reaction solution for measurement of direct bilirubin, the amount of bilirubin oxidase is reduced to a range of 0.04 to 1.2 Units/ml.

The reaction promoting agent includes, in addition to the above-mentioned potassium ferricyanide, sodium ferricyanide, potassium ferrocyanide, and sodium ferrocyanide, as well as a divalent copper ion compound such as copper sulfate, copper nitrate, copper(II) acetate, copper(II) bromide, copper(II) chloride, and the like. The reaction promoting agent is usually used in an amount of 1 to 700 mM.

The method of the present invention is generally carried out by adding a buffer containing the zinc compound and the coloring agent, and optionally the accelerator for converting indirect bilirubin into direct bilirubin to a bilirubin-containing sample, preincubating the resulting reaction solution at 25 to 45° C. for 3 to 15 minutes, usually at 37° C. for 5 minutes, adding a buffer containing bilirubin oxidase and optionally the reaction promoting agent (the buffer is referred to as enzyme reagent) to the reaction mixture, and incubating the mixture at 25 to 45° C. for 3 to 15 minutes, usually at 37° C for 5 minutes so that the reaction proceeds.

The obtained green reaction solution is then subjected to colorimetry to measure the desired bilirubin.

The colorimetry can be done by a conventional method, for example, by measuring the optical density of the reaction mixture at a wavelength of 580 nm using a commercially available spectrophotometer (e.g. UV-2100 spectrophotometer manufactured by Shimadzu Corporation, Japan) against a reagent blank. As a reference, a serum sample containing a prescribed amount (known concentration) of bilirubin (hereinafter referred to as "standard bilirubin") is used, and the optical density thereof is measured likewise. Based on the data in each measurement, the level of bilirubin in the test serum sample (mg/dl) is calculated by the following formula:

$$\text{Concentration of bilirubin (mg/dl)} = \frac{A_T}{A_{ST}} \times X \quad (I)$$

wherein $A_T$: Optical density of test serum sample
$A_{ST}$: Optical density of standard bilirubin
$X$: Concentration of bilirubin in standard bilirubin (mg/dl)

The operation for the above measurement is explained in more detail.

In case of measurement of total bilirubin, to a test serum sample is added a buffer solution (e.g. 0.1 M ACES buffer containing 0.3% sodium cholate, pH 7.0) which contains a zinc compound (e.g. 0.13 M zinc sulfate) and a coloring agent (e.g. 3 mM MBTH) as well as a prescribed amount of bilirubin oxidase and the mixture is incubated (for example, at 37° C. for 5 minutes). Alternatively, the above buffer solution containing no bilirubin oxidase is added to the test serum sample and the mixture is incubated (for example, at 37° C. for 3 minutes), and thereafter, a prescribed amount of bilirubin oxidase is added thereto and the mixture is again incubated (for example, at 37° C. for 5 minutes). The incubated mixture is then subjected to measurement of the optical density (AT) at a wavelength of 580 nm against the blank test sample. Besides, the above procedure is repeated except that standard bilirubin is used in place of the test serum sample to measure the optical density ($A_{ST}$).

In case of measurement of direct bilirubin, the above procedure and measurement is repeated except that a buffer solution of pH 3.0 to 4.5 is employed.

The reagent for measurement of bilirubin of the present invention consists of:

(i) a buffer solution containing a zinc compound, a coloring agent and optionally an accelerator for converting indirect bilirubin into direct bilirubin (referred to as coloring reagent), (ii) a buffer solution containing bilirubin oxidase and optionally a reaction promoting agent (referred to as enzyme reagent), and (iii) a serum containing a prescribed amount of bilirubin (referred to as standard bilirubin).

From the viewpoint of stability of the reagent, the reagent of the present invention is preferably in the form of a kit consisting of:

(i) a coloring agent (lyophilized),
(ii) a buffer solution for dissolving the coloring agent containing a zinc compound (i),
(iii) bilirubin oxidase (lyophilized),
(iv) a buffer solution for dissolving the enzyme (iii), and
(v) standard bilirubin (lyophilized).

According to the present invention, a stable green pigment having a large molecular extinction coefficient is formed due to the action of the zinc compound, and the bilirubin in the sample can be measured specifically. In addition, since it is not necessary to acidify the reaction solution with a strong acid after completion of the reaction, the procedure is simpler than the conventional colorimetric method, and further the accelerator for converting indirect bilirubin into direct bilirubin, which is insoluble in a strongly acidic solution, can be used and therefore the reaction of bilirubin in patient serum proceeds rapidly. This, the quantitative method and the reagent of the present invention are quite useful for clinical tests of total bilirubin and direct bilirubin in serum. The method of the present invention can be conducted simply and rapidly, and hence, is suitable designed for automatic analysis.

The reagent of the present invention and method for measuring bilirubin by the present invention are illustrated by the following Examples but should not be construed to be limited thereto.

EXAMPLE 1

Reagent for measurement of total bilirubin:

(1) First reagent:
Zinc sulfate and MBTH are dissolved in 0.1 M ACES buffer solution (pH 7.0) containing 0.3% sodium cholate so that the buffer contains 1.3 mM zinc sulfate and 3 mM MBTH.

(2) Second reagent:
Ten Units of bilirubin oxidase (derived from a species of genus *Myrothecium*) is dissolved in 0.1 M ACES buffer solution (pH 7.0) and the total volume is made to be 10 ml.

Procedure of measurement:
(i) Using Hitachi 7150 automatic analyzer, R-1 and R-2 were charged with the first reagent and the second reagent, respectively. To a test sample (10 μl) was added the first reagent in R-1 (0.3 ml) and the reaction mixture was preincubated at 37° C. for 5 minutes. Thereafter, the second reagent (0.075 ml) was added to the mixture and the reaction mixture was incubated at 37° C. for 5 minutes to proceed with the reaction. The optical density was then measured at a wavelength of 580 nm (main) and 700 nm (sub) against the reagent blank. As reference, the standard bilirubin was used and the optical density thereof was measured likewise. Based on the optical densities thus obtained, the concentration of total bilirubin was calculated in accordance with the formula (1) hereinbefore.

The absorption curve was measured by adding the first reagent (2.0) to a serum (0.1) containing direct bilirubin, preincubating the mixture at 37° C. for 5 minutes, adding the second reagent (0.5 ml) to the mixture, incubating the mixture at the same temperature for 10 minutes to proceed with the reaction, and the absorptions at 300 nm to 800 nm were measured using Shimadzu UV-2100 spectrophotometer against purified water. FIG. 1 shows the obtained absorption curve in measurement of total bilirubin. As is clear from the results shown in FIG. 1, a stable green pigment having a large molecular extinction coefficient was formed in the presence of the zinc compound and an excellent effect of the zinc compound in measurement of total bilirubin was shown.

(ii) Next, a suitable pH range of the buffer for measurement of total bilirubin was studied. The first reagents with pH 5.5, pH 6.0, pH 7.0, pH 8.0, pH 9.0 and pH 10.0 were employed. The first reagent with pH 5.5 become opaque with addition of sodium cholate as the accelerator for converting indirect bilirubin into direct bilirubin, and hence, the buffer without sodium cholate was used. The same second reagent as above was used.

Measurement was done by the same procedure as mentioned above using Hitachi 7150 automatic analyzer. Samples used for measurement were normal human serum (Seraclear N manufactured by Nippon Shoji K.K., japan), Seraclear N supplemented with powder bilirubin (indirect bilirubin manufactured by ICN, USA) and two patient sera. For comparison, measurement was also conducted in the same manner using a commercially available enzymatic reagent for measurement of total bilirubin (Nescauto T-BIL-VE, manufactured by Nippon Shoji K.K, Japan). The results are shown in Table 1.

TABLE 1

| | | Conc. of total bilirubin (mg/dl) | | | |
|---|---|---|---|---|---|
| No. | pH | Seraclear N *1 | Seraclear N suppl. with indirect bilirubin | Indirect bilirubin *2 | Patient serum (1) | Patient serum (2) |
| 1 | 5.5 | 0.5 | 8.4 | 7.9 | 6.7 | 7.5 |
| 2 | 6.0 | 0.4 | 18.6 | 18.2 | 11.2 | 14.6 |
| 3 | 7.0 | 0.4 | 19.0 | 18.6 | 11.6 | 14.5 |
| 4 | 8.0 | 0.5 | 19.2 | 18.7 | 11.4 | 14.6 |
| 5 | 8.5 | 0.4 | 19.1 | 18.7 | 11.3 | 14.3 |
| 6 | 9.0 | 0.4 | 18.8 | 18.4 | 11.5 | 14.6 |
| 7 | 10.0 | 0.2 | 11.2 | 11.0 | 8.6 | 10.3 |
| 8 | Nescauto T-BIL-VE | 0.5 | 19.1 | 18.6 | 11.7 | 14.2 |

(Note)
*1: Value of Seraclear N means bilirubin value in normal human serum
*2: Value of indirect bilirubin = (Value of Seraclear N supplemented with indirect bilirubin) − (Value of Seraclear N)

The results of Table 1 shows that nearly the same values as those measured with the commercially available reagent were obtained with the buffer at the pH range of 6.0 to 9.0 in two patient serum samples. The values of the total bilirubin concentrations in the two patient serum samples were lower when measured with the buffer at pH 5.5 This may be attributable to the absence of the agent for converting indirect bilirubin into direct bilirubin in these samples, and as a consequence, incompletion of the enzymatic reaction in 5 minutes. The lower value measured at ph 10.0 is construed to be due to inactivity of bilirubin oxidase at this pH value.

Figure 2:
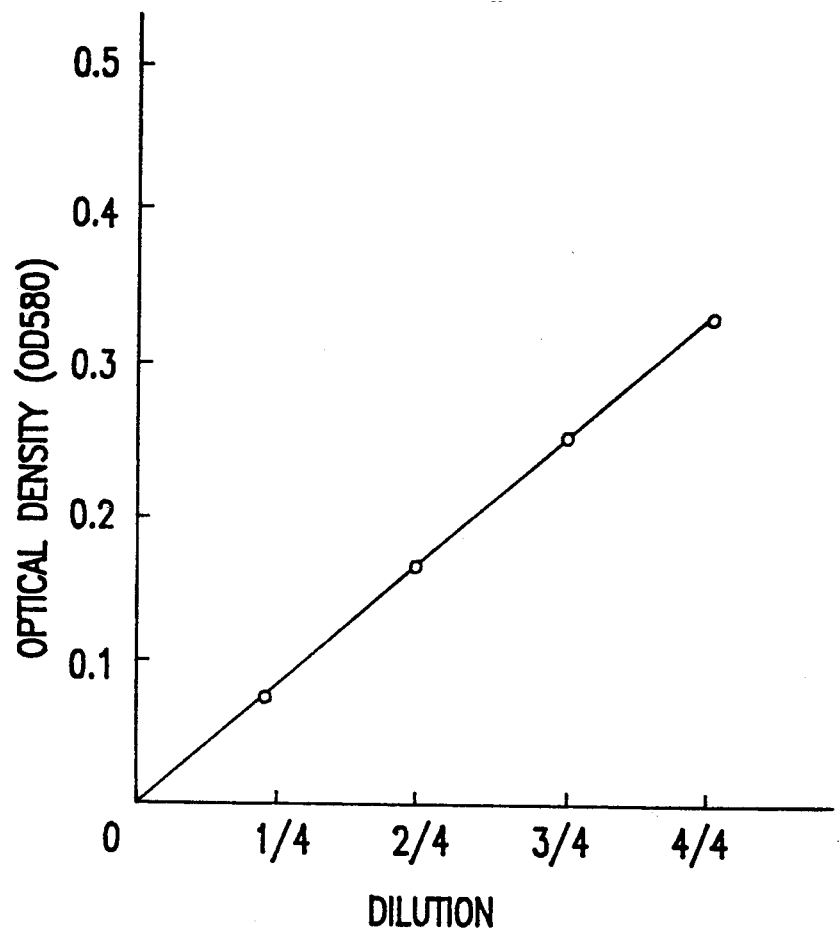
FIG. 2 is a graph showing an absorption in the measurement of total bilirubin in a standard serum which is diluted in various folds.

(iii) Besides, a standard serum (total bilirubin 14.2 mg/dl, direct bilirubin 9.2 mg/dl) was diluted in a fold of ¼, 2/4, ¾, and 4/4) and subjected to measurement with Hitachi 7150 automatic analyzer using the above reagents. The results are shown in FIG. 2. As shown in FIG. 2, a straight line passing through the origin was obtained.

EXAMPLE 2

Reagent for measurement of direct bilirubin:
(1) First reagent:
Zinc sulfate and MBTH are dissolved in 0.1 M lactic acid-sodium lactate buffer solution (pH 3.7) containing surfactants (0.1% Noigen EA-170 manufactured by Dai-ichi Kogyo Seiyaku Co. Ltd., 0.05% Emalgen manufactured by Kao Soap, Co. Ltd.) so that the buffer contains 0.9 mM zinc sulfate a 10 mM MBTH.

(2) Second reagent:
Forty Units of bilirubin oxidase (derived from a species of genus *Myrothecium*) is dissolved in 0.5 mM potassium ferricyanide solution and the total volume is made to be 10 ml.

Figure 3:
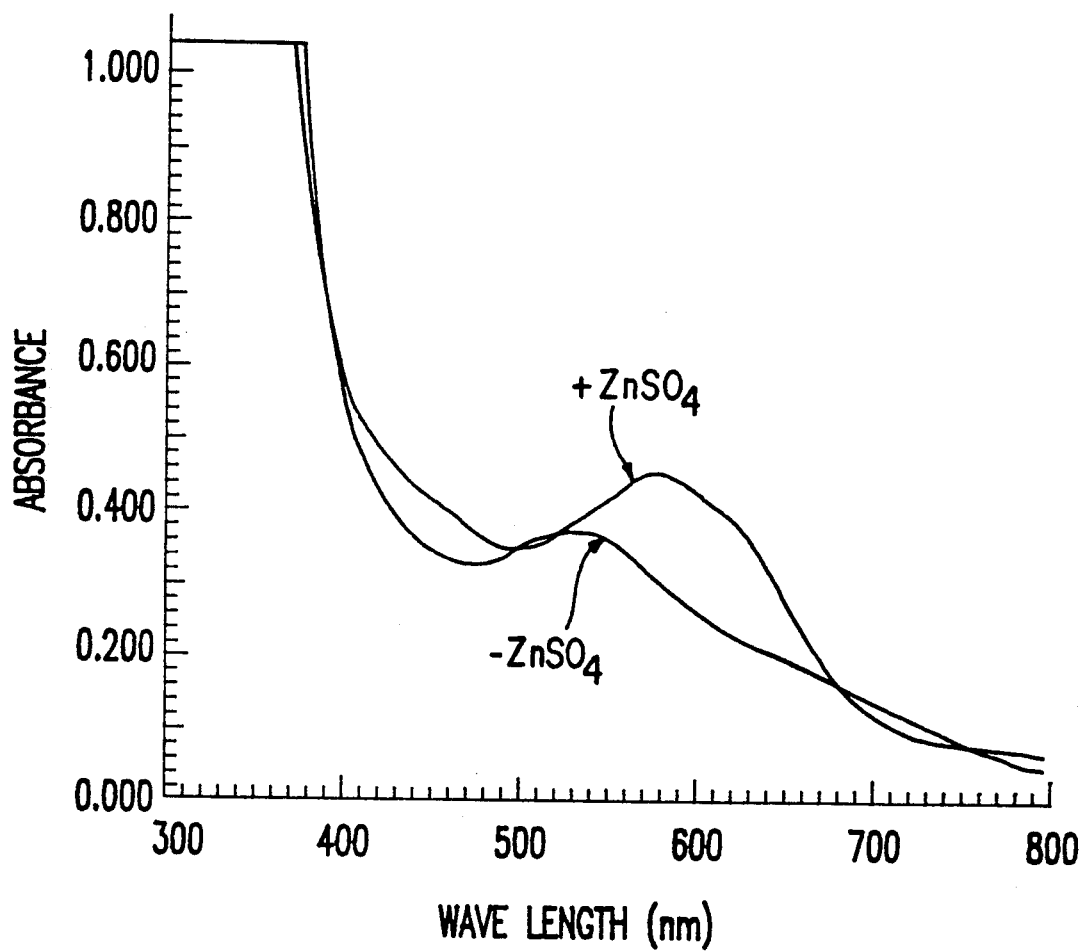
FIG. 3 is an absorption curve in measurement of direct bilirubin in a sample by the method of the present invention.

Procedure of measurement:
(i) Measurement with Hitachi 7150 automatic analyzer and measurement of absorption curve were conducted as described in Example 1. The obtained absorption curve of direct bilirubin is shown in FIG. 3. As is clear from the results shown in FIG. 3, a stable green pigment having a large molecular extinction coefficient was formed in the presence of the zinc compound and an excellent effect of the zinc compound in measurement of direct bilirubin was shown.

(ii) Next, a suitable pH range of the buffer for measurement of direct bilirubin was studied. 0.1 M tartaric acid-sodium tartrate buffer solution was employed in place of the above first reagent (0.1 M lactic acid-sodium lactate buffer solution) and was adjusted to pH 2.5, pH 3.0, pH 3.7, pH 4.0, pH 4.5 and pH 5.0. The same second reagent as above was used.

Measurement was done on normal human serum (Seraclear N, manufactured by Nippon Shoji K.K., Japan), Seraclear N supplemented with powder bilirubin (indirect bilirubin manufactured by ICN, USA) and two patient sera as described in Example 1, the procedure of measurement (ii). For comparison, measurement was also conducted in the same manner using a commercially available enzyme reagent (Nescauto D-BIL-VE, manufactured by Nippon Shoji K.K., Japan) for measurement of direct bilirubin. The results are shown in Table 2.

TABLE 2

| | | Conc. of direct bilirubin (mg/dl) | | | |
|---|---|---|---|---|---|
| No. | pH | Seraclear N *1 | Seraclear N suppl. with indirect bilirubin | Indirect bilirubin *2 | Patient serum (1) | Patient serum (2) |
| 1 | 2.5 | 0.2 | 0.2 | 0 | 4.8 | 6.2 |
| 2 | 3.0 | 0.1 | 0.1 | 0 | 4.6 | 6.2 |
| 3 | 3.5 | 0.1 | 0.1 | 0 | 4.7 | 6.1 |
| 4 | 3.7 | 0.1 | 0.1 | 0 | 4.6 | 6.1 |
| 5 | 4.0 | 0.1 | 0.1 | 0 | 4.7 | 6.2 |
| 6 | 4.5 | 0.1 | 0.1 | 0 | 4.6 | 6.1 |
| 7 | 5.0 | 0.4 | 2.8 | 2.4 | 6.8 | 7.8 |
| 8 | Nescauto D-BIL-VE | 0.1 | 0.1 | 0 | 4.6 | 6.3 |

(Note)
*1 and *2: see Table 1

As is clear from the results shown in Table 2, the concentration of direct bilirubin in the two patient serum samples measured with the buffer at pH 3.0 to 4.5 was almost the same as those measured with the commercially available enzyme reagent. The value of Seraclear N supplemented with powder bilirubin (indirect bilirubin) was the same as the value of Seraclear N at pH 2.5 to 4.5, and hence, it was confirmed that no reaction of indirect bilirubin proceeded. Although almost the same value as that measured with the commercially available enzyme reagent was obtained with the buffer at pH 2.5 in the two patient serum samples, the reason is that a blue pigment was formed in an acidic solution of pH 2.5 and the zinc compound did not effectively act at this pH. The reaction at pH 2.5 may be attributable to the effect of potassium ferricyanide which is used with bilirubin oxidase.

Figure 4:
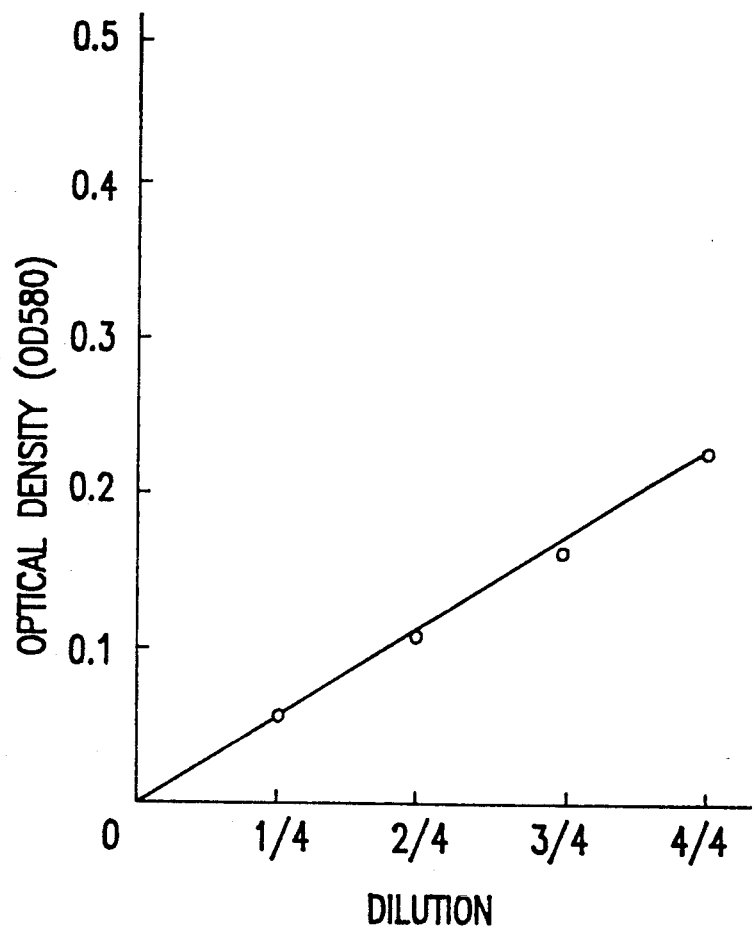
FIG. 4 is a graph showing an absorption in measurement of direct bilirubin in a standard serum which is diluted in various folds.

(iii) Besides, the standard serum was diluted (in a fold of ¼, 2/4, ¾ and 4/4) and subjected to measurement with Hitachi 7150 automatic analyzer using the above reagents for measurement of direct bilirubin. The results are shown in FIG. 4. As shown in FIG. 4, a straight line passing through the origin was obtained.

EXAMPLE 3

In the sam manner as described in Examples 1 and 2 except that 2-hydrazinobenzothiazole was used as the first reagent in place of MBTH, total bilirubin and direct bilirubin were measured respectively by measuring the absorption curve after the reaction likewise. In both measurements, a stable green pigment ($\lambda = 600$ nm) was obtained.

EXAMPLE 4

In the same manner as described in Examples 1 and 2, total bilirubin was measured by using *Trachyderma tsunodae*-origin bilirubin oxidase (10 Units/ml) in place of the second reagent in Example 1 and direct bilirubin was measured by using *Trachyderma tsunodae*-origin bilirubin oxidase (0.3 Units/ml) in place of the second reagent in Example 2, wherein the absorbance was measured at 580 nm for 10 minutes.

Powder bilirubin (indirect bilirubin) added to 5.5% human albumin reacted in measurement of total bilirubin but hardly reacted in measurement of direct bilirubin. Sera containing direct bilirubin reacted in both measurement of total bilirubin and measurement of direct bilirubin.

EXAMPLE 5

Figure 5:
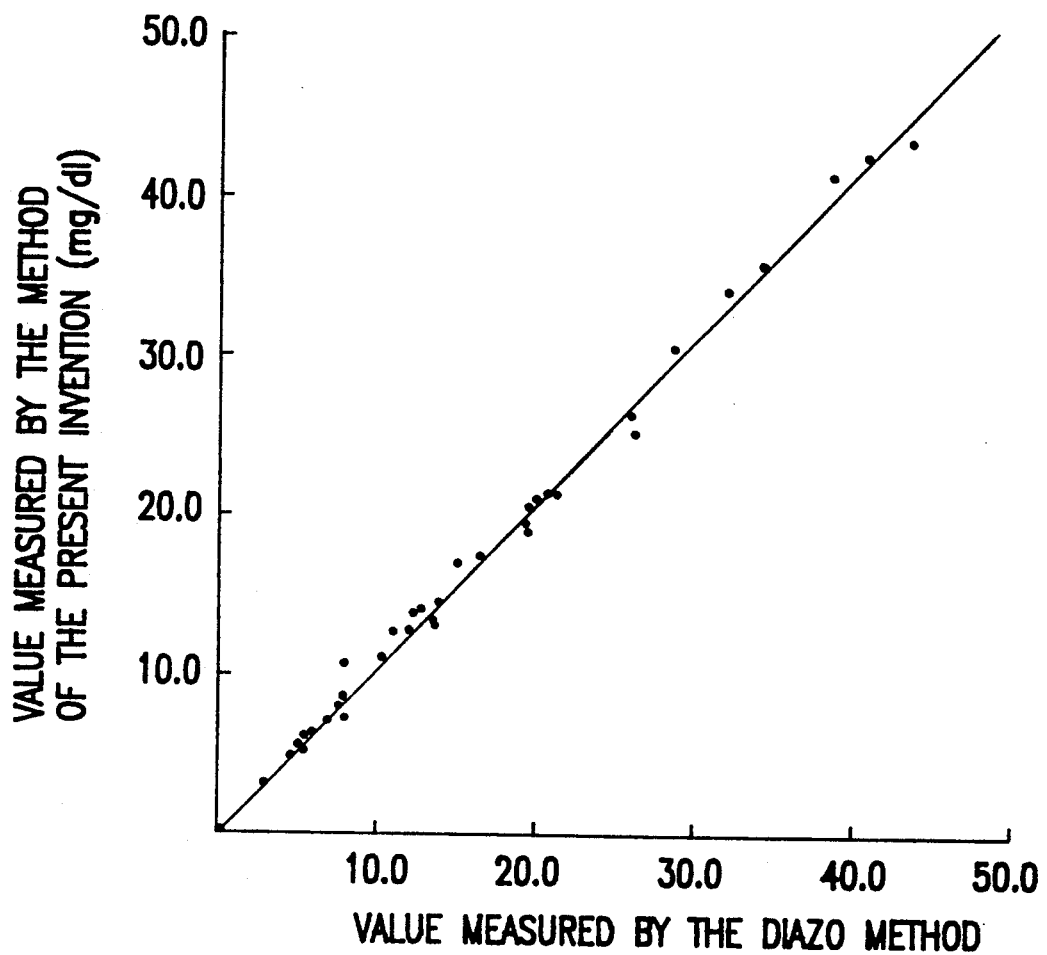
FIG. 5 is a graph showing a correlation between the total bilirubin values measured by the method of the present invention and those measured by the conventional diazo method.

(i) using hitachi 7150 automatic analyzer, the amount of total bilirubin was measured by the method for measuring total bilirubin described in Example 1 and by the commonly used diazo method (Nescauto bilirubin kit-N, manufactured by Nippon Shoji K.K., Japan). The results are depicted in FIG. 5 which shows a correlation between the values measured by the method of the present invention and the values measured by the diazo method. In FIG. 5 shows the values measured by the diazo method and Y is the value measured by the method of the present invention, and the correlation coefficient ($\gamma$) is 0.998, and there is obtained a good regression line of the formula: $Y = 1.044X + 0.005$.

Figure 6:
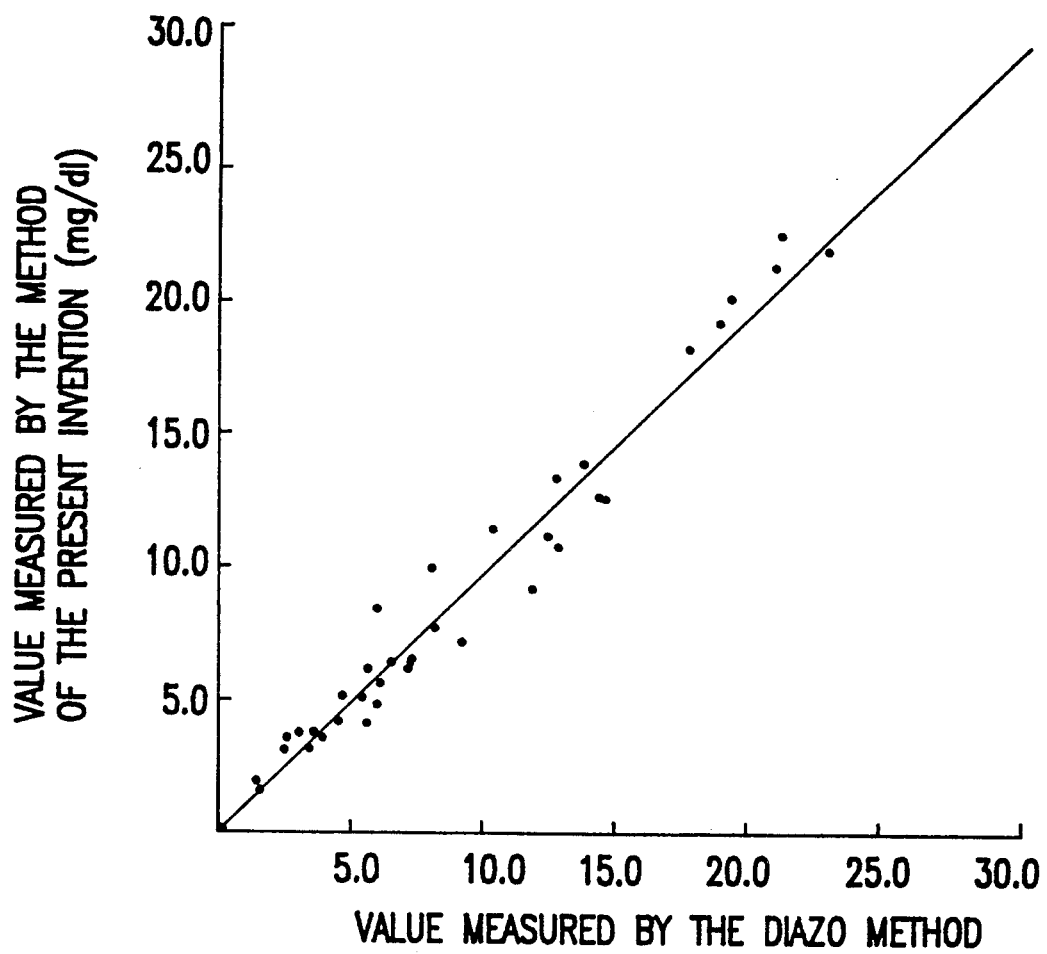
FIG. 6 is a graph showing a correlation between the direct bilirubin values measured by the method of the present invention and those measured by the conventional diazo method.

(ii) Then, the amount of direct bilirubin was measured in the same manner as described above except that 0.1 M tartaric acid-sodium tartrate (pH 3.7) was used in place of the first reagent for measuring direct bilirubin in Example 2, 0.1 M lactic acid-sodium lactate (pH 3.7). The results are depicted in FIG. 6 which shows a correlation between the values measured by the method of the present invention and the values measured by the diazo method. In FIG. 6, correlation coefficient ($\gamma$) was 0.988 and a god regression line of the formula: $Y = 0.963X + 0.061$ in which X and Y was as defined above were obtained The above results confirmed accuracy of the method of the present invention for measuring total bilirubin and direct bilirubin.

EXAMPLE 6

Various metal compounds were tested for their coloring effect in measurement of total bilirubin.

Preparation of reagents:

(1) First reagent:

Various metal compounds (see Table 3 and FIG. 7) and MBTH are dissolved in 0.1 M MOPSO buffer solution (pH 6.5) so that the buffer contains 1.6 mM metal compound (0.1 mM for zinc oxide which is hard to dissolve in water) and 1 mM MBTH.

(2) Second reagent:

Forty Units of bilirubin oxidase (derived from a species of *Myrothecium*) are dissolved in 0.1 M MOPSO buffer solution (pH 6.5) and the total volume is made to be 10 ml.

Procedure of measurement:

To a serum sample containing direct bilirubin (0.1 ml) was added to first reagent (2.0 ml) and the mixture was preincubated at 37° C. for 5 minutes. To the mixture was then added the second reagent (0.5 ml) and the mixture as incubated at 37° C. for 10 minutes to proceed with the reaction, followed by measurement of an absorption curve at 300 to 800 nm against purified water using Shimadzu UV-2100 spectrophotometer. The results are shown in the following Table 3 and FIG. 7.

TABLE 3

| Metal compound | Result | Metal compound | Result |
|---|---|---|---|
| Zinc sulfate | o | Ferrous chloride | x |
| Zinc chloride | o | Ferrous sulfate | x |
| Zinc acetate | o | Iron (III) ammonium sulfate | x |
| Zinc oxide | o | Iron (III) ammonium oxalate | x |
| Cadmium chloride | x | Potassium bromide | x |
| Cadmium sulfate | x | Sodium hydrosulfite | x |
| Beryllium sulfate | x | Calcium sulfate | x |
| Beryllium hydroxide | x | Nickel chloride | x |
| Barium fluoride | x | Cobalt acetate | x |
| Barium chromate | x | Cobalt (III) acetylacetonate | x |
| Copper acetate | x | Titanic sulfate | x |
| Potassium ferricyanide | x | Ceric sulfate | x |
| Potassium ferrocyanide | x | Manganese chloride | x |
| Strontium sulfate | x | Sodium tungstate | x |
| Copper sulfate | x | Sodium fluoride | x |
| Lithium sulfate | x | Magnesium chloride | x |

(Note)
o: Colored pigment is shifted to a long-wave length.
x: Colored pigment is not shifted to a long-wave length.

Figure 7:
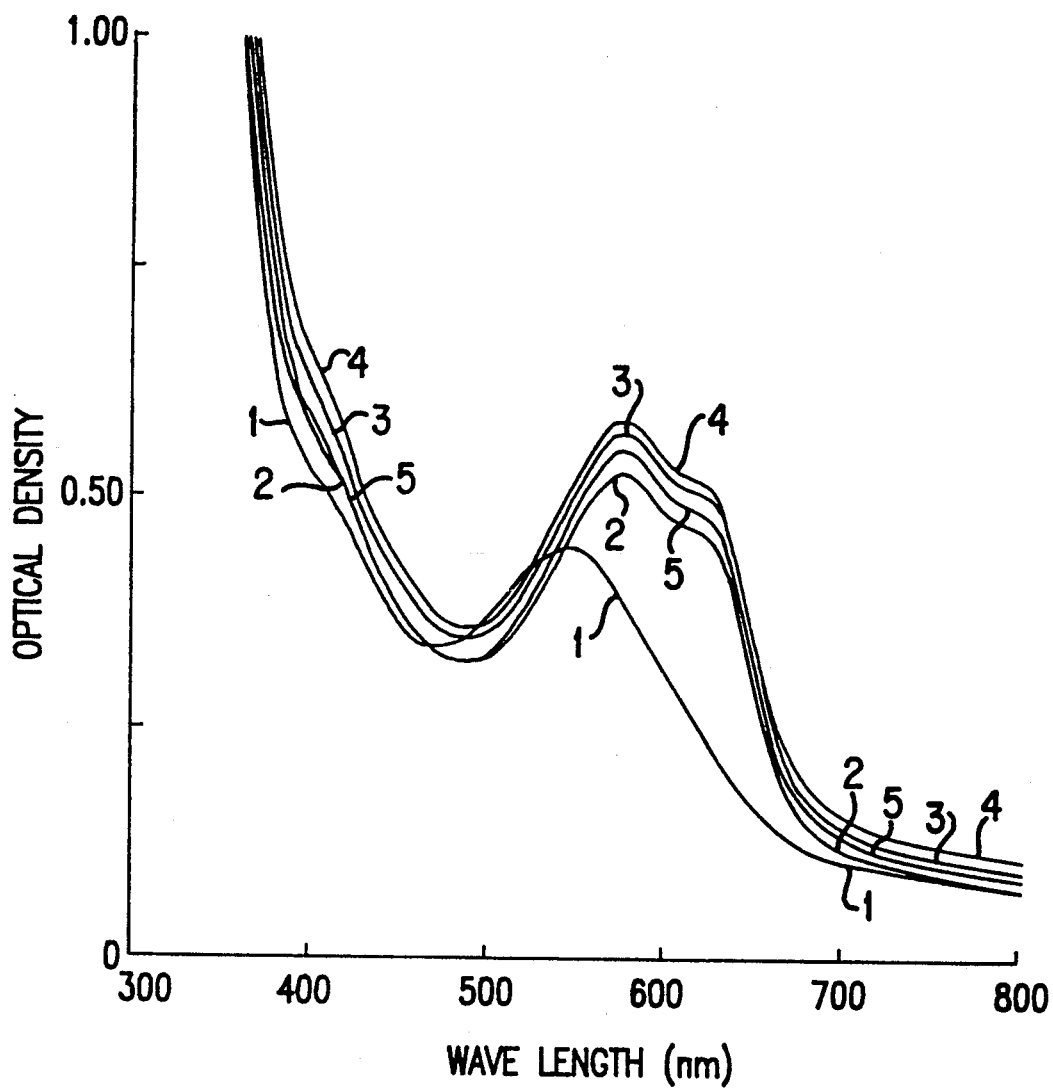
FIG. 7 shows absorption curves in measurement of total bilirubin by the method of the present invention using a variety of zinc compounds.

As is clear from the results shown in Table 3 and FIG. 7, only the zinc compounds could form a stable green pigment having a large molecular extinction coefficient, confirming the effect of the zinc compounds. Compounds of other metals of the same group as zinc (i.e. cadmium, beryllium, barium, etc.) showed no effect.

What is claimed is:

1. A method for optical measurement of bilirubin which comprises reacting a bilirubin-containing sample with a zinc compound, bilirubin oxidase in a buffer and a coloring agent selected from the group consisting of 3-methyl-2-benzothiazolinone-hydrazone, 2-hydrazinobenzothiazole, and 1-hydrazinophthalazine hydrochloride.

2. The method of claim 1 wherein a total bilirubin is measured by using a buffer of pH 6.0 to 9.0.

3. The method of claim 1 wherein a direct bilirubin is measured by using a buffer of pH 3.0 to 4.5.

4. The method of claim 1 wherein the zinc compound is at least one zinc compound selected from the group consisting of a zinc oxide, a zinc salt of an inorganic acid, a zinc salt of an organic acid, a zinc halogenide and a zinc cyanide.

5. The method of claim 2 wherein the buffer is selected from Good's buffers.

6. The method of claim 3 wherein the buffer is selected from the group consisting of tartaric acid-sodium tartrate buffer, lactic acid-sodium lactate buffer, glycine-hydrochloric acid buffer, acetic acid-sodium acetate buffer and sodium acetate-hydrochloric acid buffer.

7. A reagent for measurement of bilirubin which comprises a buffer containing a zinc compound and a coloring agent selected from the group consisting of 3-methyl-2-benzothiazolinone-hydrazone, 2-hydrazinobenzothiazole, and 1hydrazinophthalazine hydrochloride, and a buffer containing bilirubin oxidase.

8. The reagent of claim 7 which is for measurement of total bilirubin wherein the buffer is selected from Good's buffer of pH 6.0 to 9.0.

9. The reagent of claim 7 which is for measurement of direct bilirubin wherein the buffer is selected from the group consisting of tartaric acid-sodium tartrate buffer, lactic acid-sodium lactate buffer, glycine-hydrochloric acid buffer, acetic acid-sodium acetate buffer and sodium acetate-hydrochloric acid buffer.

* * * * *